(12) United States Patent
Oliver

(10) Patent No.: US 12,144,662 B2
(45) Date of Patent: Nov. 19, 2024

(54) SURGICAL INSTRUMENT ORGANIZER

(71) Applicant: Rashae Deanna Oliver, Leesburg, GA (US)

(72) Inventor: Rashae Deanna Oliver, Leesburg, GA (US)

( * ) Notice: Subject to any disclaimer, the term of this patent is extended or adjusted under 35 U.S.C. 154(b) by 0 days.

(21) Appl. No.: 18/163,570

(22) Filed: Feb. 2, 2023

(65) Prior Publication Data

US 2024/0261054 A1    Aug. 8, 2024

(51) Int. Cl.
*A61B 50/20* (2016.01)

(52) U.S. Cl.
CPC .................. *A61B 50/20* (2016.02)

(58) Field of Classification Search
CPC ...... A61B 50/20; A61B 50/22; B65D 25/107; B65D 25/101; B65D 25/103; B65D 25/10
USPC ....... 211/69, 70.7, 70.6, 85.13, 40; 206/369, 206/371, 370, 477, 478, 480; 248/68.1; D24/229, 230; D8/356
See application file for complete search history.

(56) References Cited

U.S. PATENT DOCUMENTS

| | | | | |
|---|---|---|---|---|
| 2,868,389 | A | * | 1/1959 | Friend ................ A47G 25/1471 211/123 |
| D199,504 | S | * | 11/1964 | Maiolatesi ..................... 118/500 |
| 3,285,768 | A | * | 11/1966 | Habib ................. B29C 44/5636 428/167 |
| 3,367,483 | A | * | 2/1968 | Studen ............... B65D 81/1075 217/27 |
| 3,487,947 | A | * | 1/1970 | Bogar, Jr. .............. A01K 97/08 211/89.01 |
| 3,696,920 | A | * | 10/1972 | Lahay ..................... A61B 50/30 206/370 |
| 3,819,039 | A | * | 6/1974 | Erickson .......... A61B 17/06061 428/167 |
| 4,243,140 | A | * | 1/1981 | Thrun .................... A61B 50/31 206/460 |
| 4,498,938 | A | * | 2/1985 | Moisson .................. H01R 4/70 156/49 |
| 4,548,328 | A | * | 10/1985 | Brauning ................. A47F 7/24 211/205 |
| 4,760,929 | A | * | 8/1988 | Fedorchak ............... A47F 7/24 211/105.1 |
| 4,791,752 | A | * | 12/1988 | Van Kampen ......... A01K 97/06 242/402 |
| 4,971,271 | A | * | 11/1990 | Sularz ..................... F16L 3/223 248/68.1 |
| 5,005,710 | A | * | 4/1991 | Hofer ...................... B25H 3/04 D6/567 |
| 5,046,624 | A | * | 9/1991 | Murphy ................. A61B 50/20 D24/227 |
| D321,249 | S | * | 10/1991 | Gorski ........................ D24/229 |

(Continued)

*Primary Examiner* — Jennifer E. Novosad

(74) *Attorney, Agent, or Firm* — Dunlap Bennett & Ludwig PLLC; Anna L. Kinney

(57) ABSTRACT

A surgical instrument organizer includes a foam tube and double-sided adhesive. The tube has a bore through it, a longitudinal slit parallel to the bore and extending from an outer surface of the foam tube to the bore; and multiple parallel grooves perpendicular to the bore. The grooves have a depth greater than a radius of the tube. The adhesive extends along a length of the tube on an external surface opposite the grooves. The organizer keeps instruments aligned and neat makes sure all personnel are safe from sharps.

3 Claims, 4 Drawing Sheets

(56) References Cited

U.S. PATENT DOCUMENTS

| | | | | |
|---|---|---|---|---|
| 5,201,430 A * | 4/1993 | Artzer | A47G 21/14 | 206/370 |
| 5,224,596 A * | 7/1993 | Kruger | A61M 5/3213 | 206/366 |
| 5,358,111 A * | 10/1994 | Greenberg | A61B 17/06161 | 604/263 |
| 5,387,177 A * | 2/1995 | Dunn | A61G 7/07 | 5/655 |
| 5,411,141 A * | 5/1995 | Bounds | A47G 21/14 | 248/37.3 |
| 5,447,243 A * | 9/1995 | Graber | B43M 99/008 | 211/13.1 |
| D366,814 S * | 2/1996 | Stroecker | D7/641 | |
| 5,542,550 A * | 8/1996 | Kakavoulis-Perera | G11B 33/0483 | 211/163 |
| D378,408 S * | 3/1997 | Pyeatt | D8/356 | |
| 5,643,217 A * | 7/1997 | Dobkin | A61B 17/00 | 604/174 |
| 5,960,957 A * | 10/1999 | Johnson | A47F 5/0823 | 206/338 |
| 6,092,675 A * | 7/2000 | Ramirez, Jr. | A63D 15/10 | 473/44 |
| 6,167,914 B1 * | 1/2001 | Koteskey | E21B 43/086 | 138/156 |
| 6,203,654 B1 * | 3/2001 | McFall | A61F 13/15707 | 156/308.2 |
| D442,007 S * | 5/2001 | Lin | D6/682.4 | |
| 6,360,051 B1 * | 3/2002 | Daoud | G02B 6/4471 | 385/136 |
| 6,458,104 B2 * | 10/2002 | Gautsche | A61B 46/23 | 604/179 |
| 6,491,067 B1 * | 12/2002 | Davenport | H02G 3/0468 | 138/156 |
| 6,520,348 B1 * | 2/2003 | Bulusu | H01L 21/67313 | 211/41.18 |
| 7,303,568 B2 * | 12/2007 | Jannot | A61B 17/06061 | 606/148 |
| 7,571,819 B2 * | 8/2009 | Reeves | G11B 33/0444 | 211/41.12 |
| 7,744,572 B2 * | 6/2010 | Bierman | A61M 25/02 | 206/366 |
| 8,069,998 B2 * | 12/2011 | Thomas | A61B 50/34 | 206/370 |
| 8,162,156 B1 * | 4/2012 | Crisman | G10D 13/12 | 211/85.6 |
| 9,402,494 B1 * | 8/2016 | O'Brien | A47F 7/19 | |
| D774,002 S * | 12/2016 | Hsieh | D13/155 | |
| 10,300,248 B2 * | 5/2019 | Taylor | A61M 25/02 | |
| 10,492,596 B2 * | 12/2019 | Pegues | A45D 44/02 | |
| D930,459 S * | 9/2021 | Breines | D8/356 | |
| 11,191,603 B1 * | 12/2021 | Schor | A47B 81/00 | |
| 11,712,317 B2 * | 8/2023 | Reeves | A61B 50/20 | 211/205 |
| 11,826,537 B2 * | 11/2023 | Roddy | A61M 39/08 | |
| 2001/0035384 A1 * | 11/2001 | Davis | A61B 50/20 | 206/370 |
| 2003/0132352 A1 * | 7/2003 | Weaver | A61G 7/0503 | 248/68.1 |
| 2004/0222175 A1 * | 11/2004 | Keating | A61B 50/20 | 211/85.13 |
| 2006/0076254 A1 * | 4/2006 | Corbitt | A61B 50/22 | 206/370 |
| 2006/0237597 A1 * | 10/2006 | D'Andria | F16B 3/223 | 248/51 |
| 2011/0253845 A1 * | 10/2011 | Bianco | A47G 21/14 | 248/37.3 |
| 2012/0091289 A1 * | 4/2012 | Tomlinson | F16L 3/13 | 248/65 |
| 2012/0216385 A1 * | 8/2012 | Taylor | A61M 25/02 | 428/156 |
| 2016/0066997 A1 * | 3/2016 | Ren | A61B 50/20 | 211/85.13 |
| 2019/0191910 A1 * | 6/2019 | Davis | A47B 61/003 | |
| 2024/0261054 A1 * | 8/2024 | Oliver | A61B 50/20 | |

* cited by examiner

SURGICAL INSTRUMENT ORGANIZER

BACKGROUND OF THE INVENTION

The present invention relates to surgical instruments and, more particularly, to a surgical instrument organizer.

In the operating room, surgical technicians used rolled up sterile towels to keep instruments straight and aligned, e.g., on a Mayo stand (a removable instrument tray set on a movable stand). However, the towels flatten out during the procedure, which causes the instruments to fall over.

As can be seen, there is a need for a surgical instrument organizer.

SUMMARY OF THE INVENTION

In one aspect of the present invention, a surgical instrument organizer comprises a foam tube characterized by having a bore formed therethrough; a longitudinal slit parallel to the bore and extending from an outer surface of the foam tube to the bore; and a plurality of parallel grooves perpendicular to the bore, having a depth greater than a radius of the foam tube; and double-sided adhesive extending along a length of the foam tube on an external surface opposite the plurality of parallel grooves.

The inventive instrument organizer enables surgical techs to keep their instruments aligned and neat while on the Mayo stand, as well as making sure all personnel are safe from sharps.

These and other features, aspects and advantages of the present invention will become better understood with reference to the following drawings, description, and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a surgical instrument organizer. The inventive organizer may be sterilized, used in the sterile environment, then thrown away after the surgical procedure.

The foam roll is generally cylindrical, with a longitudinal passage or bore that is open at both ends.

A slit on the underside may extend from one end of the roll to the other through the longitudinal passage. Suture ties may be placed in the slit.

Closely adjacent grooves, for example about 10 or more, may be cut into the top surface of the foam roll down to the longitudinal passage. The grooves support surgical instruments.

Double-sided tape may be applied along the length of the roll on the underside thereof to keep the foam roll in place on a surface during use.

To manufacture the inventive instrument organizer, the manufacturer may cut a longitudinal slot through the thickness of a tubular foam roll, for example with a knife. The manufacturer may apply two-sided tape longitudinally along an exterior of the tube, proximate to the longitudinal slot. The manufacturer may then cut grooves into the foam tube diametrically opposite the two-sided tape and transverse to the central passage. The grooves may be any suitable depth, such as at least the radius of the foam tube while not passing through the longitudinal slot.

To use the inventive organizer, the foam roll may be removed from a sterile package. The technician or surgeon may remove the backing from the double-sided tape and may place the roll on the Mayo stand with the tape face down. If surgical ties are used for the procedure, they may be slid inside the long slit on the bottom side of the roll so that they hang out the two ends of the roll. The instruments to be used may be placed through the slits on the instrument roll. The slits keep the instruments upright while on the Mayo stand, keeping the Mayo stand clean and organized.

Figure 1:
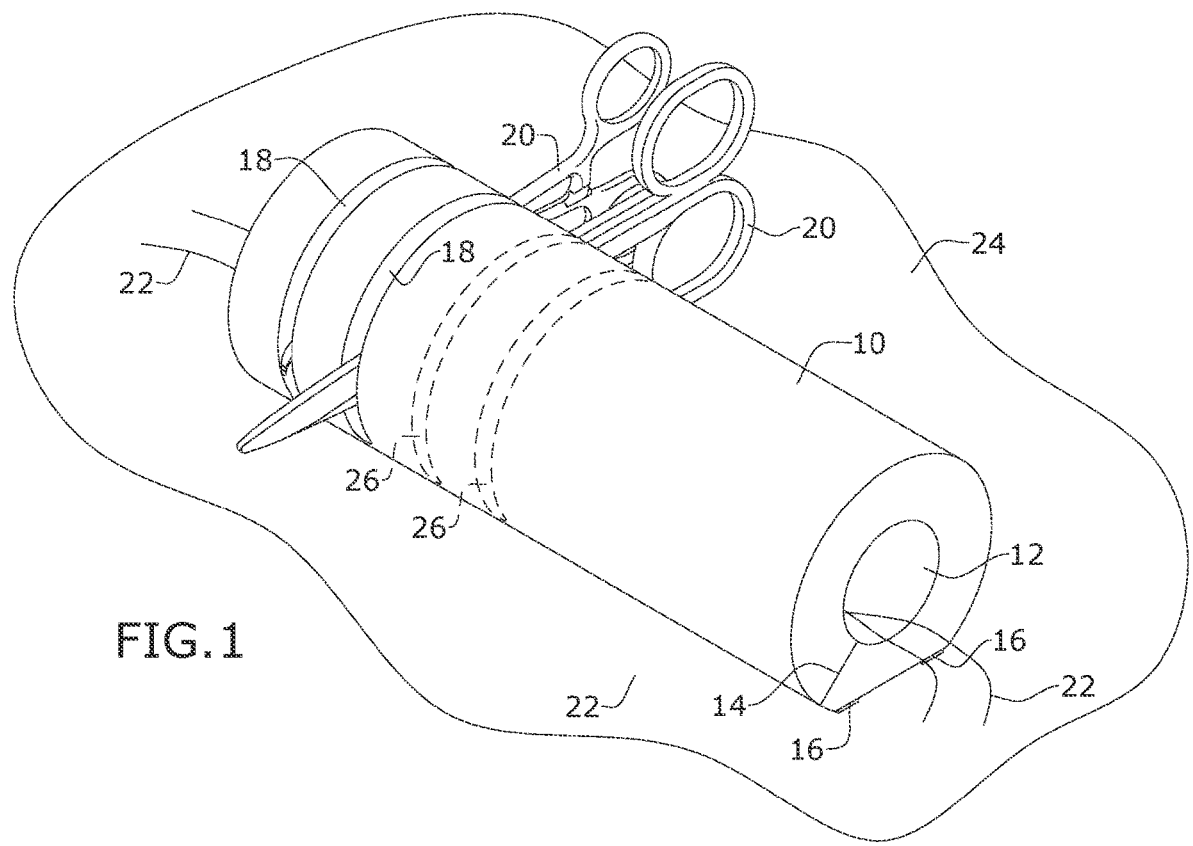
FIG. 1 is a perspective view of a surgical instrument organizer, shown in use.
Figure 2:
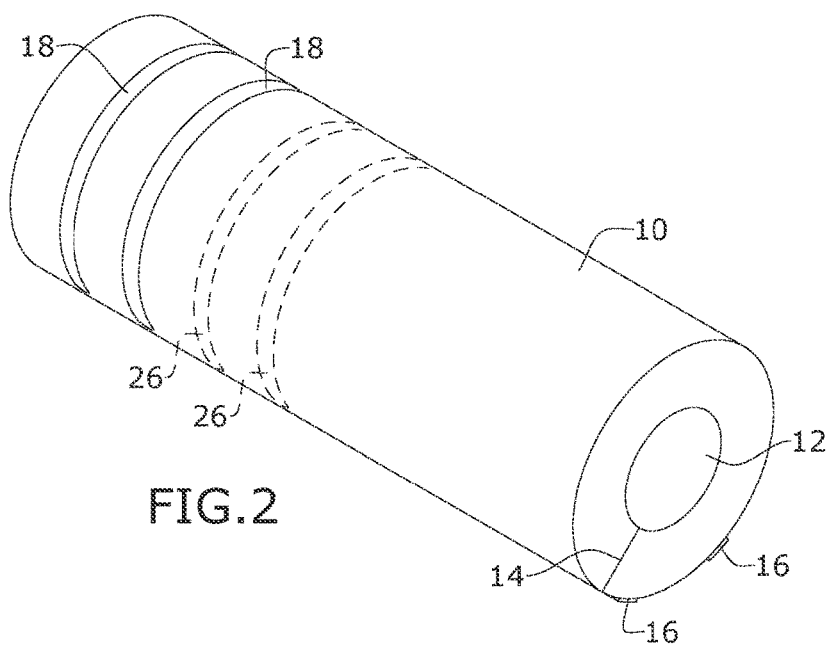
FIG. 2 is another perspective view thereof.
Figure 3:
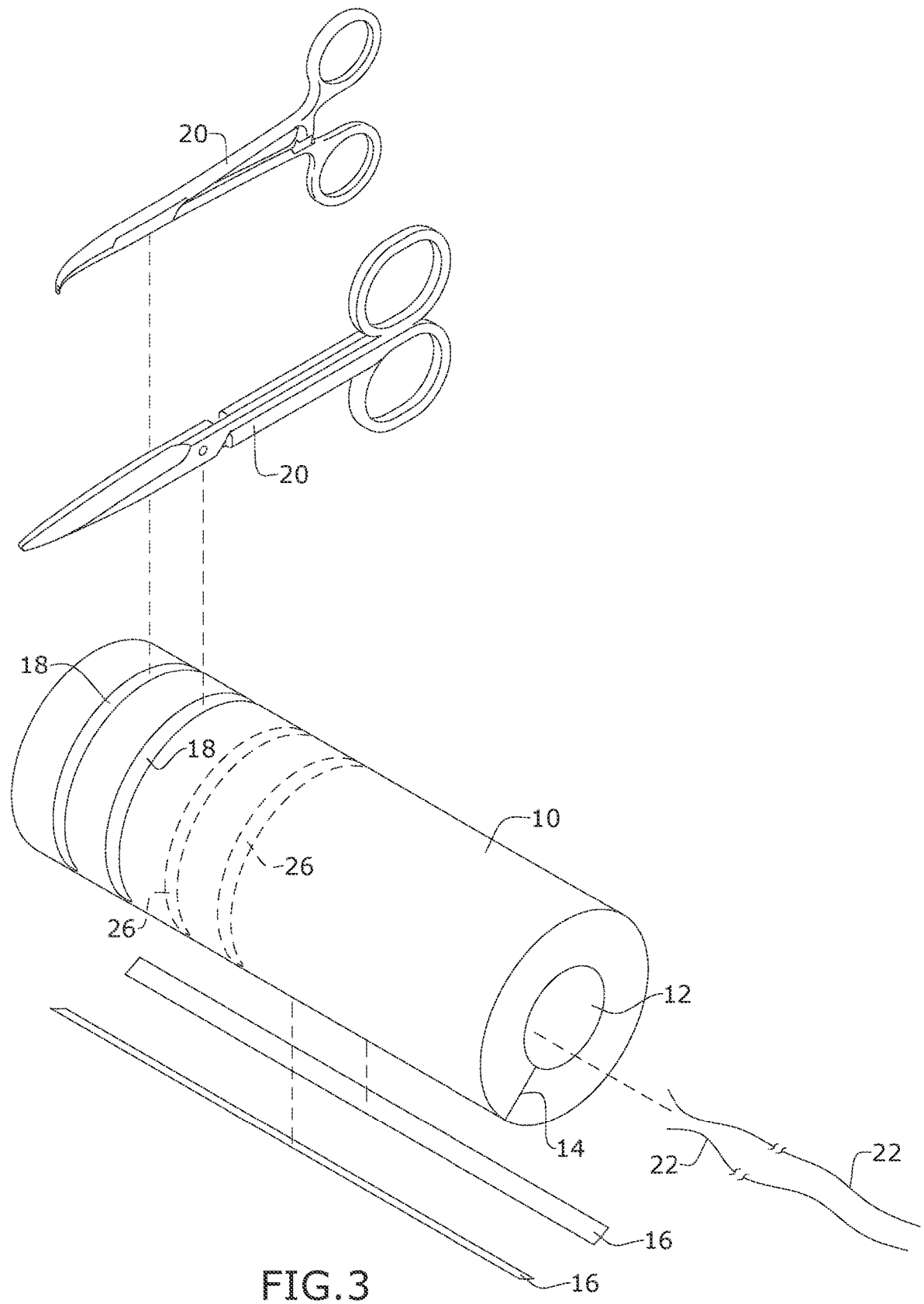
FIG. 3 is an exploded view thereof.
Figure 4:
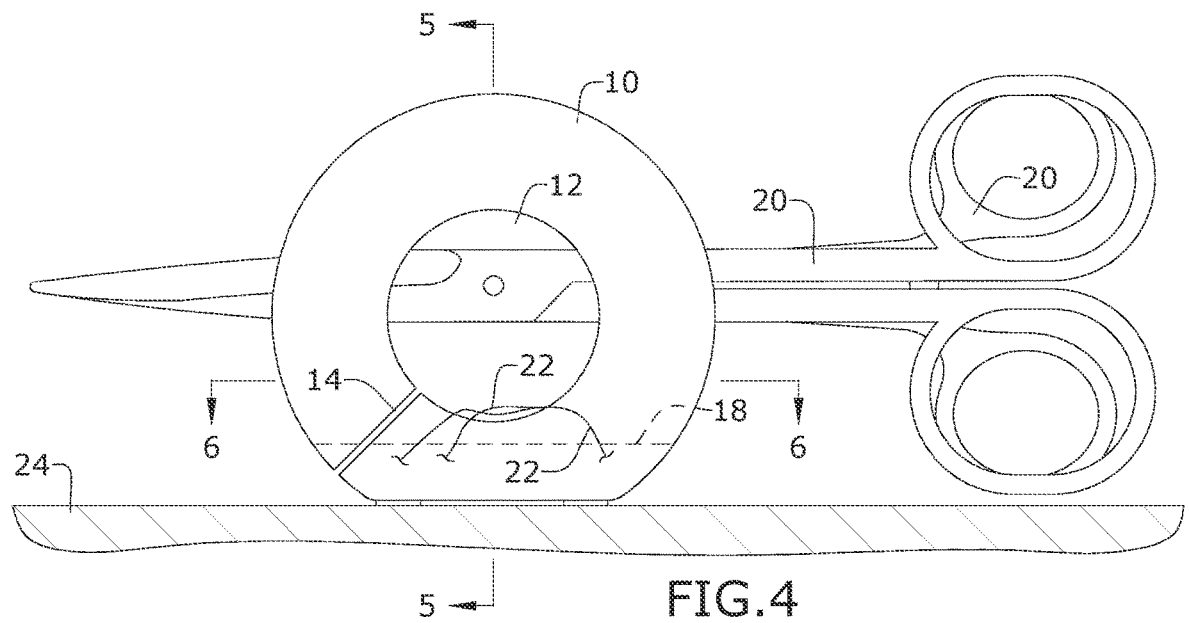
FIG. 4 is a right-side elevation view thereof, shown in use.
Figure 5:
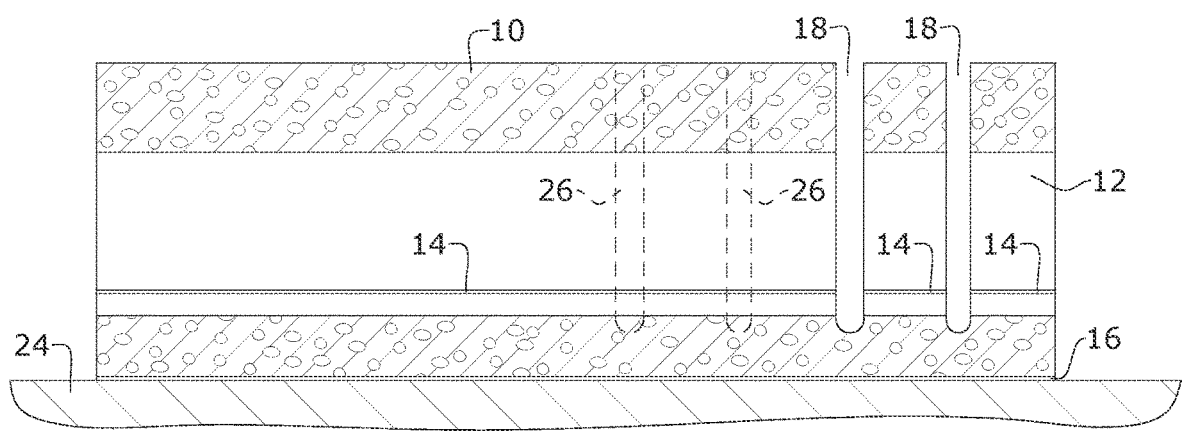
FIG. 5 is a sectional view thereof, taken along line 5-5 from FIG. 4.
Figure 6:
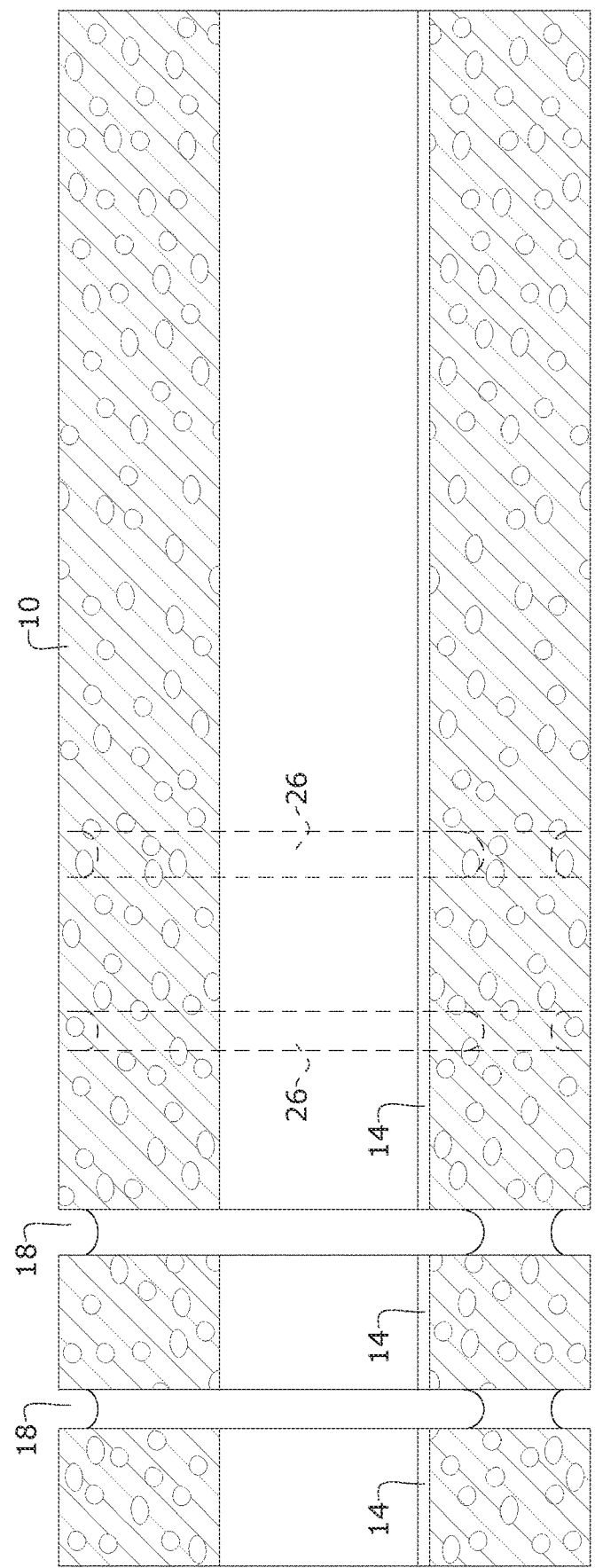
FIG. 6 is a sectional view thereof, taken along line 6-6 from FIG. 4.

Referring to FIGS. 1 through 6, FIGS. 1 and 2 illustrate a foam tube 10 according to an embodiment of the present invention. An opening, bore, or longitudinal passage 12 extends through the foam tube 10 from end to end. A slit 14 extends from an exterior surface of the foam tube 10 into and along the full length of the longitudinal passage 12. Suture ties 22 may be stored within the longitudinal passage 12 by sliding the ties 22 through the slit 14, as shown in FIG. 3. Double-sided adhesive tape 16 extends along the length of the foam tube 10, affixing the tube 10 to a mounting surface 24. As shown, two parallel lengths of tape 16 may be provided, with one length of tape 16 proximate to the slit 14. A plurality of groove openings 18 may be formed perpendicular to the longitudinal passage 12 and additional slots 26 may be cut according to the quantity of instruments 20 to be supported. FIGS. 4-6 further illustrate the groove openings 18 and slots 26. The instruments 20 may be lowered into the groove openings 18 prior to use, as seen in FIG. 3.

As shown in FIGS. 4 and 5, the groove openings 18 may extend beyond the central passage, into the lower portion of the tube 10. The groove 18 length is substantially equal to the tube 10 diameter, is generally greater than its depth, and both the length and depth are generally greater than the groove 18 width.

It should be understood, of course, that the foregoing relates to exemplary embodiments of the invention and that modifications may be made without departing from the spirit and scope of the invention as set forth in the following claims.

What is claimed is:

1. A surgical instrument organizer, comprising:
a foam tube characterized by having a bore formed therethrough; a longitudinal slit parallel to the bore and extending from an outer surface of the foam tube to the bore; and a plurality of parallel grooves perpendicular to the bore, having a depth greater than a radius of the foam tube; and
double-sided adhesive extending along a length of the foam tube on an external surface opposite the plurality of parallel grooves.

2. The surgical instrument organizer of claim 1, wherein the foam tube is sterile.

3. The surgical instrument organizer of claim 1, wherein the foam tube is disposable.

* * * * *